United States Patent [19]

Borah et al.

[11] Patent Number: 4,755,045
[45] Date of Patent: Jul. 5, 1988

[54] METHOD AND SYSTEM FOR GENERATING A SYNCHRONOUS DISPLAY OF A VISUAL PRESENTATION AND THE LOOKING RESPONSE OF MANY VIEWERS

[75] Inventors: Joshua D. Borah, Mansfield; James C. Merriam, West Newton, Jose Velez, Brookline, of Mass.

[73] Assignee: Applied Science Group, Inc., Waltham, Mass.

[21] Appl. No.: 931,234

[22] Filed: Nov. 17, 1986

Related U.S. Application Data

[63] Continuation-in-part of Ser. No. 848,154, Apr. 4, 1986.

[51] Int. Cl.$^4$ .......................... A61B 3/14; A61B 3/00; G03B 29/00
[52] U.S. Cl. .................................... 351/210; 351/206; 354/62
[58] Field of Search ................................ 351/209, 210

[56] References Cited

U.S. PATENT DOCUMENTS

| | | |
|---|---|---|
| 3,473,868 | 10/1969 | Young et al. . |
| 3,507,988 | 4/1970 | Holmes ............................. 351/210 |
| 3,542,457 | 11/1970 | Balding ............................ 351/210 |
| 3,583,794 | 6/1971 | Newman . |
| 3,594,072 | 8/1971 | Feather et al. . |
| 3,623,799 | 11/1971 | Millodot . |
| 3,679,295 | 8/1972 | Newman et al. . |
| 3,689,135 | 9/1972 | Young et al. . |
| 3,984,156 | 10/1976 | Jernigan .......................... 351/209 |
| 4,034,401 | 7/1977 | Mann ................................. 351/210 |
| 4,075,657 | 2/1978 | Weinblatt ......................... 351/210 |

FOREIGN PATENT DOCUMENTS

| | | | |
|---|---|---|---|
| 125808A | 4/1983 | European Pat. Off. ............ | 351/210 |
| 157973A | 10/1985 | European Pat. Off. ............ | 351/209 |
| 2103045A | 2/1983 | United Kingdom ................ | 351/209 |
| 1215656 | 2/1986 | U.S.S.R. ............................... | 351/209 |

OTHER PUBLICATIONS

Eye Movements & the High Psychological Functions, 1978, Lawrence Erlbaum-pub, pp. 65-75, by Sheena & Flagg.
Eye Movements-Cognition & Visual Perceptions, 1981, Lawrence Erlbaum-pub, pp. 257-268, by Sheena & Borah.
Eye Movement Measurement Techniques by Young and Sheena, from American Psychologist, vol. 30, #3, Mar. 1975, pp. 315-330.
Methods & Design-Survey of Eye Movement Recording Methods, Behavior Research Methods & Instrumentation, 1975, vol. 7(5), pp. 397-429.
Eye-Trac Catalog by ASL, copyright 1982.

Primary Examiner—Rodney B. Bovernick
Assistant Examiner—Jay P. Ryan
Attorney, Agent, or Firm—Body, Vickers & Daniels

[57] ABSTRACT

A method and system for generating a dynamic, real time synchronized display of individual visual fixation points of one or more viewers superimposed on a video taped visual presentation for subsequent evaluation to assess the effectiveness of such visual presentation in communicating information.

32 Claims, 8 Drawing Sheets

○ MALE
▲ FEMALE

METHOD AND SYSTEM FOR GENERATING A SYNCHRONOUS DISPLAY OF A VISUAL PRESENTATION AND THE LOOKING RESPONSE OF MANY VIEWERS

This is a continuation-in-part of application Ser. No. 848,154 filed 4-4-86 and currently pending before the United States Patent and Trademark Office.

The present invention relates to the art of evaluating the effectiveness of visual presentations such as television commercials and more particularly to a method and apparatus for generating a simulataneous display of the looking response of many viewers superimposed upon a video taped presentation.

INCORPORATION BY REFERENCE

The full disclosure of currently pending U.S. patent application Ser. No. 848,154 is hereby incorporated by reference.

Further, as background information, the following publications are hereby incorporated by reference: Semiautomatic Eye Movement Data Analysis Technique for Experiments with Varying Scenes, David Sheena and Barbara N. Flagg, Eye Movements and the Higher Psychological Functions, 1978, Publisher Lawrence Erlbaum, pages 65-75; Compensation for Some Second Order Effects to Improve Eye Position Measurements, David Sheena and Joshua Borah, Eye Movements—Cognition and Visual Perceptions, 1981, Publisher Lawrence Erlbaum, pages 257-268; Eye Movement Measurement Techniques, Lawrence R. Young, David Sheena, American Psychologist, Vol. 30, No. 3, March 1975, pages 315-329; Methods & Design—Survey of Eye Movement Recording Methods, Behavior Research Methods & Instrumentation, 1975, Vol. 7(5), pages 397-429; eye-trac catalog by ASL (Applied Science Laboratories, a division of A. S. Laboratories, Inc.), copyright 1982.

BACKGROUND

Evaluating audio-visual presentations such as television commercials for effectiveness in communicating information to human viewers has been approached in a number of ways. Originally, such evaluations were performed only by individuals who were considered to have specialized knowledge or abilities which enabled them to predict the effectiveness of such presentations. These personalized evaluations have indeed continued and, in fact, many such individuals are employed as staff personnel or independent consultants by advertising agencies, marketing oriented corporations, publishing houses and the like. The shortcomings of such personal evaluations lie in the fact that they are necessarily subjective. Indeed, they are based on artistic interpretations which are highly subject to individual variation.

In attempts to obtain more objective analysis, many advertising agencies, publishing houses and corporations have adopted policies of using committees or panel discussion groups for the evaluations of television commercials and other visual or audio-visual presentations. After viewing a subject presentation separately or in groups, such group members discuss the effectiveness of various aspects or objects contained in the subject presentation. These group techniques are widely acceptable although, here again, their subjectiveness is well recognized and is largely thought to be due to the natural psychological tendency of individuals, whether alone or in groups, to respond in the manner believed to be sought by their interviewer, as opposed to responding in a truly objective manner. Additionally, such group session techniques are extremely expensive.

Most recently, efforts in this area have been directed to the development of truly objective methods of assessing the effectiveness of video presentations. These efforts have been greatly facilitated by the development in the mid 1960's of certain eye monitoring devices capable of tracking the movement of the eye and recording its point of gaze relative to a specific visual stimulus. The most popular and original eye movement monitoring device of this type was the Limbus eye monitor disclosed in U.S. Pat. No. 3,473,868, Young. Numerous improvements to this rudimentary device have been effected and are illustrated in U.S. Pat. Nos. 3,583,793, Newman; 3,594,072, Feather; 3,623,799, Millodot; 3,679,295, Newman; and 3,689,135, Young. Many of these eye monitoring instruments are described in the various publications which have been incorporated by reference herein.

The most advanced eye monitoring instrument presently available employs a technique whereby a beam of light is projected onto the corneal surface of an eye of a viewing individual. A video camera is aligned coaxially with the beam of light so as to monitor the viewing individual's eye pupil. The pupil appears as a bright disk since the camera actually detects the illuminator beam reflected from the retina back through the pupil aperture. The reflection of the light-beam from the surface of the cornea appears as an even brighter spot to the video camera. Thus, the video camera continually monitors the pupil and corneal reflection. The length and direction of the vector from the center of the pupil to the corneal reflection is continuously computed by signal processing instrumentation. These values are in turn used to continuously compute eye line-of-gaze. This technique is used by the ASL Model No. 1998 Eye Movement Monitor System (Applied Science Laboratories, Waltham, Mass.) which is the most advanced eye movement monitor system presently available. For purposes of clarity, this method of eye monitoring will hereinafter be referred to as the "pupil centercorneal reflection" technique.

Despite the commercial availability of sophisticated pupil center-corneal reflection monitoring equipment such as the ASL Model No. 1998, the commercial application of such equipment has largely been limited to the evaluation of static materials such as print advertising and still photographs. In fact, the use of such eye monitoring equipment to evaluate dynamic, video taped presentations such as television commercials has not been widely accepted because by the prior art the cost of processing and analyzing the large amounts of machine readable data generated by such evaluations would have been prohibitive. Indeed, it was not until the invention disclosed in U.S. patent application Ser. No. 848,154, hereinafter referred to as Ser. No. 848,154 and incorporated herein by reference, that the use of eye monitoring equipment in the evaluation of dynamic video tape presentations such as television commercials could be effected reliably and economically.

The invention disclosed in Ser. No. 848,154 relates to a method and apparatus for generating, recording, processing, formating, displaying and evaluating eye monitor generated data obtained from individuals watching video taped presentations. Generally, the inventive concept disclosed in Ser. No. 848,154 involves the use of readily available equipment, in a novel combination, to generate the distribution of actual looking time of individuals viewing a subject presentation (i.e. a television commercial). By the method of Ser. No. 848,154, the distribution of actual looking time is arrived at by first displaying the presentation to an individual while such individual is stationed within a visually neutral room wherein extraneous distractions are minimized or eliminated. An eye monitoring device employing the pupil center-corneal reflection method is used to record the subject individual's point of gaze at intervals of one-thirtieth of a second or faster. Thus, the data so generated consists of a large series of discrete eye position points. These data points encompass periods of eye "fixation" as well as intervals of eye movement termed "saccades". It is, however, only during periods of eye fixation that the viewing individual will perceive and assimilate information. Accordingly, the method of Ser. No. 848,154 separates "fixation" data from less informative "saccadic" data. The method records fixation point parameters such as: starting time, duration and X, Y coordinates of each such visual fixation. The X, Y coordinates so defined are, of course, in spacial relationship to the video presentation shown the subject individual. These fixation parameters are then recorded in a storage file. By recording only the fixation parameters and discarding the less valuable data relating to periods of visual saccades, the amount of data to be stored is minimized and, thus, the method becomes more commercially feasible.

Having obtained these visual fixation data, the visual presentation is then edited into a series of individual scenes, each scene having a real time duration. Specific areas of interest within each scene are then chosen and their boundaries defined by specific X, Y coordinates. Of course, the length of each scene is determined by the number of frames in which the various areas of interest remain substantially unchanged in their X, Y coordinates or contents. Alternatively, or additionally, the scene duration may be defined by the beginning and/or completion of an overlying audio signal.

By the method of Ser. No. 848,154, the starting time, duration and spacial boundaries of each area of interest contained in a given scene are then recorded on a data file. Each scene data storage file is then compared to the corresponding fixation point data file to produce a third data file in which the visual fixation data obtained from each test individual is correlated with the specific areas of interest contained in each scene. After repeating this process for all the individuals so subjected to this testing procedure, a group data file is produced. From these group data a mean distribution of looking time is generated for each area of interest within each scene. Such group data files are felt to contain truly objective information indicating the actual looking behavior of the subject individuals.

The method of Ser. No. 848,154, as summarized above, is limited to specific scenes, each of which contain defined areas of interest. Thus, the method of Ser. No. 848,154 necessitates a significant amount of film or video tape handling in order to delineate the selected areas of interest and to segment the presentation into scenes of specific duration.

In addition, the data display and method of Ser. No. 848,154 relates only to the predesignated areas of interest. If, retrospectively, one desires to sub-divide a previously defined area of interest in order to differentiate between objects contained within such area, reprocessing of the data is necessary. Thus, even by the method disclosed in Ser. No. 848,154, the evaluation of dynamic video presentations remains somewhat expensive, cumbersome and time consuming. This drawback is unfortunate in view of the highly objective nature of such eye movement data.

THE INVENTION

The present invention obviates the need for delineating specific areas of interest and the need for segmenting the presentation into finite scenes through the provision of a real time synchronized display of fixation point data superimposed upon a video tape of the subject presentation. Thus, the central concept of the present invention relates to a method and system whereby points of visual fixation are determined from individuals viewing a visual presentation and then plotted, at discrete time intervals. Thus, a real time synchronized graphic display of significant visual fixation points is obtained. Such graphic plot is then superimposed thereon, indicating individual points of visual fixation.

In accordance with the present invention, there is provided a method and system for generating a real time synchronized display of the looking response of many viewers superimposed upon a video taped presentation. The looking response data so displayed consists of an X, Y mapping of individual eye fixations determined from raw eye movement data recorded by the pupil center-corneal reflection technique. As such, the fixation point data displayed by the method of the present invention is highly objective and largely devoid of psychological and personal bias. Also, by extracting individual fixation points from the raw eye movement data, the amount of data to be stored and analyzed is reduced.

The method and system of the present invention involves four general steps (1) stimulus presentation and raw data collection, (2) data processing, (3) video taping of results, and (4) evaluation. The first step of stimulus presentation and raw data collection is effected in the manner described in U.S. patent application Ser. No. 848,154 incorporated herein by reference and discussed above. Accordingly, the stimulus presentation and raw data collection takes place in a visually neutral viewing room having no obtrusive cameras, lights or technical equipment which would in any way influence the eye movement of the individual or the individual's ability to concentrate and perceive. No head supports, chin rests or goggles are used. The elimination of such paraphernalia is advantageous as such tends to detract from the visual neutrality of the viewing room.

The method and system of the present invention further involves the second step of data processing whereby the raw eye movement data is converted into a series of eye fixations, each such fixation being defined by its start time, duration and X, Y position coordinates. These data are then reformatted to facilitate transfer and storage in retrievable form and also to expedite the plotting of the fixation coordinates by computer graphics. All fixation points are plotted in real time synchrony with the stimulus video. Thus, the fixation coordinate plot is updated at predetermined intervals (i.e. every fourth frame of the stimulus video) and only those fixations which are present at each such predetermined interval are plotted. Real time synchrony of the stimulus video and the graphic display is maintained through the use of a display driver circuit. The display driver circuit first receives a starting signal which marks the beginning of the stimulus video. Such starting signal may consist of a simple audio tone, such as a "beep" emitted by a second audio channel of the video tape device replaying the stimulus video. After being triggered by the start signal, the display driver circuit then derives vertical synchronizing pulses from the video signal, such vertical synchronizing pulses being used to trigger a counter which, upon each predetermined number of pulses (i.e. every eighth pulse--2 fields/frame x 4 frames), will generate an electrical signal. Upon sensing of such signal, an appropriately programmed computer will cause the proper set of fixation coordinates to be displayed graphically, such coordinates will remain so displayed until the next signal received from the counter causes plotting of new coordinates. This dynamic, graphic display of visual fixation points is readily storable on video tape.

In accordance with a still further aspect of the present invention, the third step consists of mixing and video taping a real-time synchronized composite display of the dynamic visual fixation point plot superimposed upon a video tape of the stimulus visual presentation. Thus, the fixation point plot is superimposed upon the video stimulus to provide a dynamic video taped display for ready evaluation. After having recorded, selected and displayed the fixation data, such data is optically or electronically combined with the stimulus video presentation to provide a permanent record of the fixation data/video stimulus composite. In this manner, the advantages of video taping, such as ease of production, variable play back speed, ability to stop/start playback, and the ready availability of equipment are fully realized.

To record the fixation point display superimposed on the subject video, either an electronic or optical method may be used. By the electronic method, a video/computer mixer may be employed as a means for overlaying the fixation plot and the video material that the subject was viewing. Alternatively, by the optical method, a beam splitting plate glass (i.e. Edmund Scientific Cat. No. 72502) is positioned at a 45° angle between two perpendicularly positioned video monitors such that the image from one monitor reflects from the beam splitter to an appropriately positioned video camera while the image from the other monitor passes through the beam splitter to the same camera. By this method, the video camera will simultaneously record the image from the monitor displaying the real time synchronized fixation point plot and the image from the monitor displaying the subject visual presentation.

Further, in accordance with the invention, the composite display of visual fixation points superimposed upon the presentation viewed by the subject is evaluated to determine the effectiveness of this presentation. The evaluation may be carried out by the vendor of the process or by the buyer depending on application and where the experience lies. In evaluating advertising materials such as television commercials, it will be advisable for the individual conducting the evaluation to have a current understanding of scientific methods of interpreting looking response, since the application of eye movement behavior to advertising marketing is a novel approach. In carrying out such evaluation, it is desirable to identify objects on the stimulus video which generate high interest (i.e., those upon which the majority of fixation points are concentrated). In this manner, one may identify those objects on the subject presentation which generate the highest interest. If the objects so identified are indeed those which the maker of the presentation intended to be of interest (such as the product to be sold in a television commercial) the evaluation will have confirmed the potential effectiveness of the presentation. If, however, the intended objects of interest are not so identified, it may be advisable to alter the presentation in order to redirect viewer attention. For example, it often happens that certain elements unintentionally generate a great deal of interest thus distracting from other elements of the presentation. When such is the case, the present invention allows the evaluator to identify the detracting elements with relative ease. Additionally, the present invention enables the evaluator to analyze the interest generated by moving objects as well as those which remain stationary during particular scenes of the presentation. By the method and system of the present invention, objects in motion are followed by concentrated "swarms" of fixation points which move along with the object. Moreover, the evaluator may determine if specific textual materials or other written matter has been read as the fixation points will appear to move along such written text.

The principal object of the invention is to provide an objective and commercially feasible method and system for evaluating the contents of visual or audiovisual presentations for effectiveness in communicating information to human viewers. By the present invention, the viewing behavior of the subject individuals is presented dynamically, in real time synchrony with the visual or audio-visual presentation. Thus, the evaluation process is simplified in that it does not require that the stimulus presentation be edited into individual scenes or segmented specific areas of interest.

A further object of the present invention is to provide a method and system for processing raw eye movement data generated in response to a visual stimulus to obtain a real time synchronized plot of fixation points and to superimpose such fixation points upon a video tape of the original visual stimulus.

Still a further object of the present invention is to provide a system whereby the moment to moment response of a group of viewing individuals is displayed in a time synchronized manner which facilitates easy evaluation of the content of a visual or audio-visual presentation for effectiveness in communicating information to the viewing individuals.

Yet another object of the present invention is to provide a method and system for the ready display and analysis of looking response relative to moving objects.

Yet another object of the present invention is to render known methods of recording eye movement, such as the corneal reflection-pupil center technique commercially feasible and objectively reliable as means for evaluating visual and audio-visual presentations such as television commercials. Prior to the present invention, the data generated by such eye monitoring equipment was voluminous, and even with the advent of methods to reduce raw eye movement data to specific fixation coordinates, the display of such coordinates for evaluation, required extensive manual endeavors. The present invention overcomes these time consuming and limiting steps, thereby rendering the concept of instrumental eye monitoring a commercially exploitable and valuable tool for the analysis of viewing response and the evaluation of visual and audio-visual presentations for effectiveness in communicating information.

Still another object of the present invention is to provide a method and system whereby the audio portion of an audiovisual presentation may be evaluated to determine its effects on the looking response of individuals watching the visual portion of such audiovisual presentation.

A still further object of the present invention is to provide a method and system whereby the looking response to various subgroups within a viewer sample may be readily evaluated for trends in looking response which may be peculiar to or lacking in particular subclass. To wit: The dynamic, graphic display of individual fixation points may be displayed such that the points derived from one group are distinguishable from those of other viewers. For example, the fixation points of males may be displayed as round dots while those of females may be displayed as triangles. Or, where color graphics are employed, color may be used to differentiate between viewer subgroups.

Thus, the present invention is a useful means for evaluating video taped materials such as television commercials for effectiveness in communicating specific information. If, by the method of the present invention, it is determined that the desired information is not being communicated effectively, the subject commercial may be edited or altered so as to more precisely achieve the desired communication goals. Because the present invention provides a real time synchronized display of visual fixation data superimposed upon the subject presentation, there is provided a simple means for evaluating the moment to moment viewing response of viewing individuals. In contrast to the prior art, this novel means of displaying visual fixation data enables analysis of looking response to moving objects as well as those which remain stationary for significant periods of time.

Further, by the system of the present invention, individual visual fixation points are displayed as darkened circles superimposed directly on a video tape or video display of the subject presentation. There is no need for delineation of specific areas of interest. Therefore, one need not predefine the visual objects. In fact, under the method of the present invention, one may learn that a particular visual object is surprisingly attractive to viewers and, accordingly, the commercial may be redesigned or rewritten to take advantage of such fortuitous observation.

These objects and advantages, as well as the discussed attributes of the present invention, and others, are obtained and will be apparent from the following description taken together with the accompanying drawings which show a preferred embodiment of the present invention.

BRIEF DESCRIPTION OF THE DRAWINGS

Referring now to the drawings wherein the showings are for the purpose of illustrating a preferred embodiment of the invention only and not for the purposes of limiting same, FIG. 1 shows scene A of a television commercial or video scene or picture wherein a human FIG. 1 is depicted holding a sample product 2 while standing in front of a mountain range 3. Fixation data points are superimposed upon the scene as dark dots 4. Thus, the majority of visual fixation points shown are centered on or near the sample product 2 while a lesser number are in the area of the face of the human FIG. 1 and a singular fixation point is superimposed upon the background mountains 3.

FIG. 2 depicts four separate frames of a video presentation depicting a moving aircraft 8. Again, visual fixation points are depicted as dark dots. Thus, FIG. 2 illustrates the manner in which the visual fixation points of many individual viewers will follow a moving object of primary interest in a swarm-like pattern 10.

FIG. 3 shows a block diagram of a preferred embodiment of the present invention whereby a video taped television commercial is presented 12 to an individual or individuals. The eye movement of one or more viewing individuals is monitored 13 during presentation of the video taped commercial. From the eye movement measurements so obtained, specific fixation point data is extracted 14 for each test individual. The variables extracted for each such fixation include starting time, duration and X Y coordinates. These fixation variables are then stored in retrievable form relative to time 15. After compiling a file of fixation point data 15 obtained from the desired number of viewing individuals, such data are then graphically displayed relative to time as a dynamic fixation point plot 16. Real time synchrony between the video taped commercial and the dynamic graphic display of fixation points is achieved by rerunning the video taped commercial 17 and deriving therefrom, by means of a display driver circuit, a series of vertical sync pulses. These vertical sync pulses are then used to trigger replotting of the graphic display 16 at real time synchronized intervals 19. The video images of the rerun commercial 17 and the dynamic graphic display of fixation points 16 are then mixed by either electronic or optical means to obtain a composite display 21 of the commercial and the graphic display of fixation points. This composite display may, of course, be evaluated directly. However, as a practical matter, it is desirable to record a video tape 22 of the composite display and to subsequently evaluate such composite video tape 23.

Figure 1:
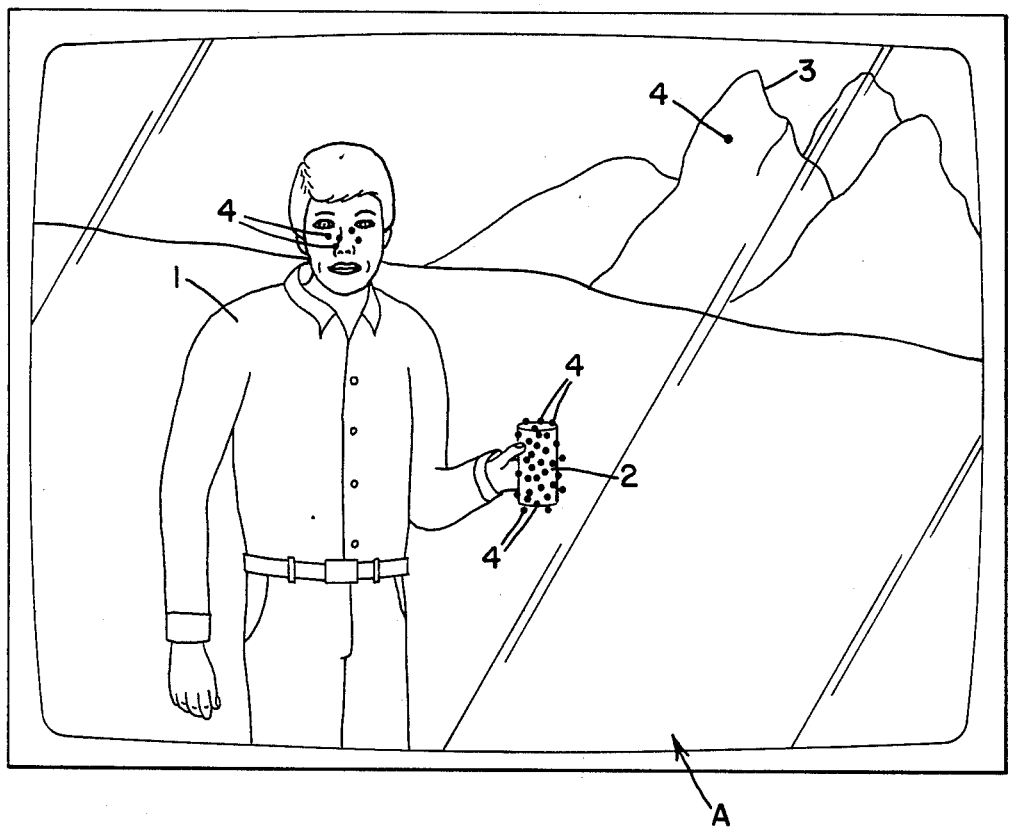
FIG. 1 is a view of a single scene from a television commercial with individual visual fixation points represented by darkened dots superimposed upon the scene itself.
Figure 2A:
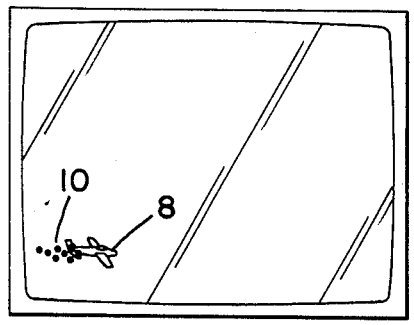
FIG. 2 is a four frame view of a moving object with visual fixation data represented by darkened points following the travel of such moving object in a swarm-like pattern.
Figure 2B:
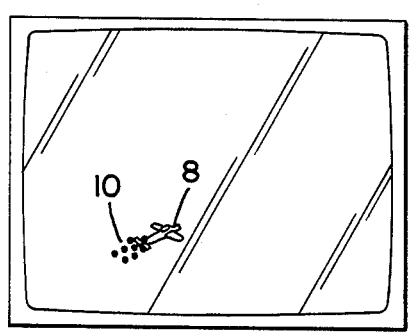
Figure 2C:
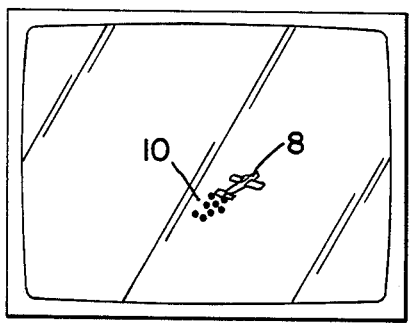
Figure 2D:
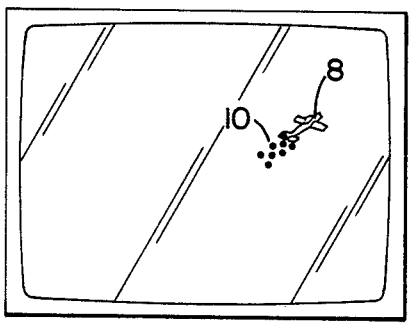
Figure 3:
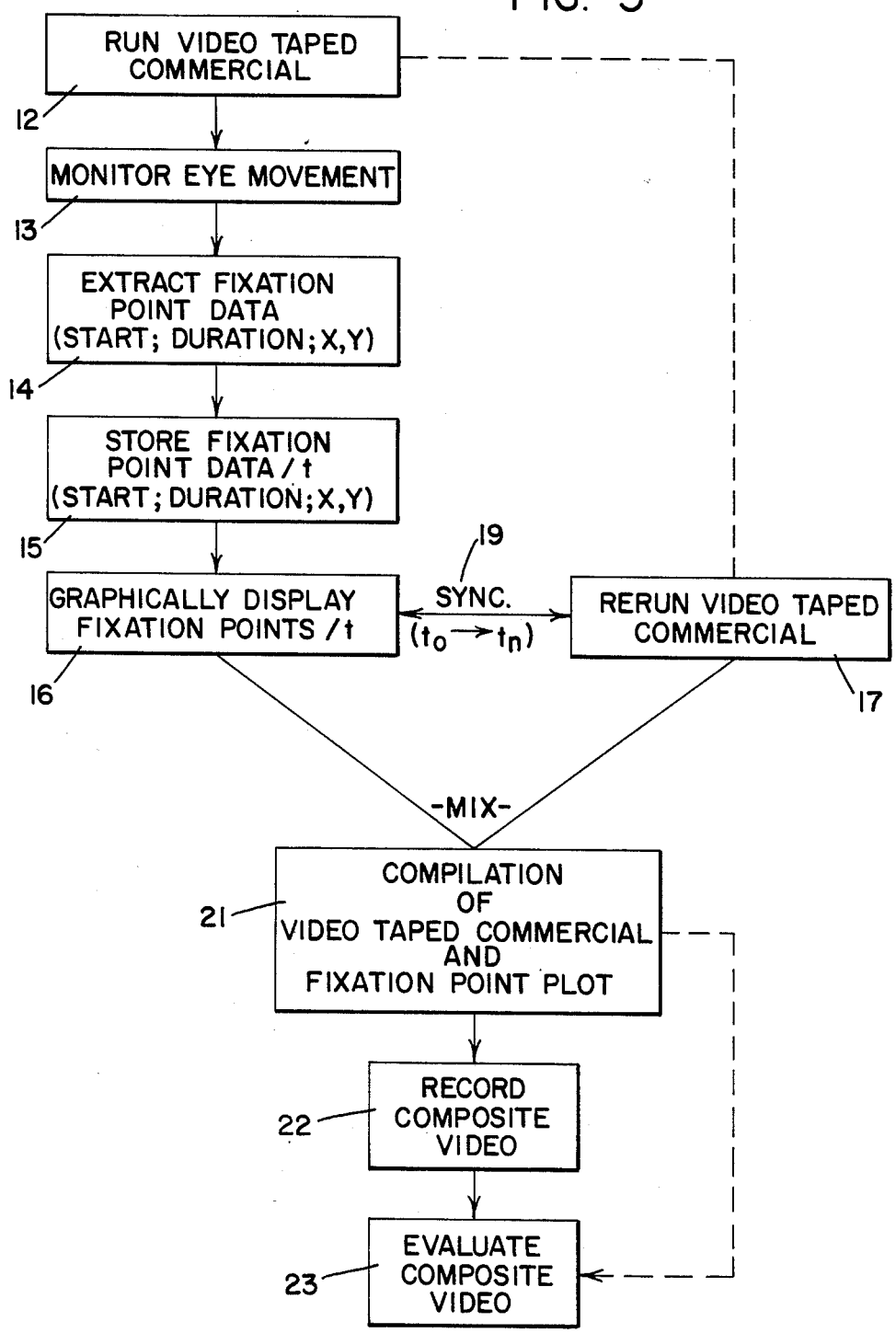
FIG. 3 is a block diagram illustrating the general method of the present invention.
Figure 4:
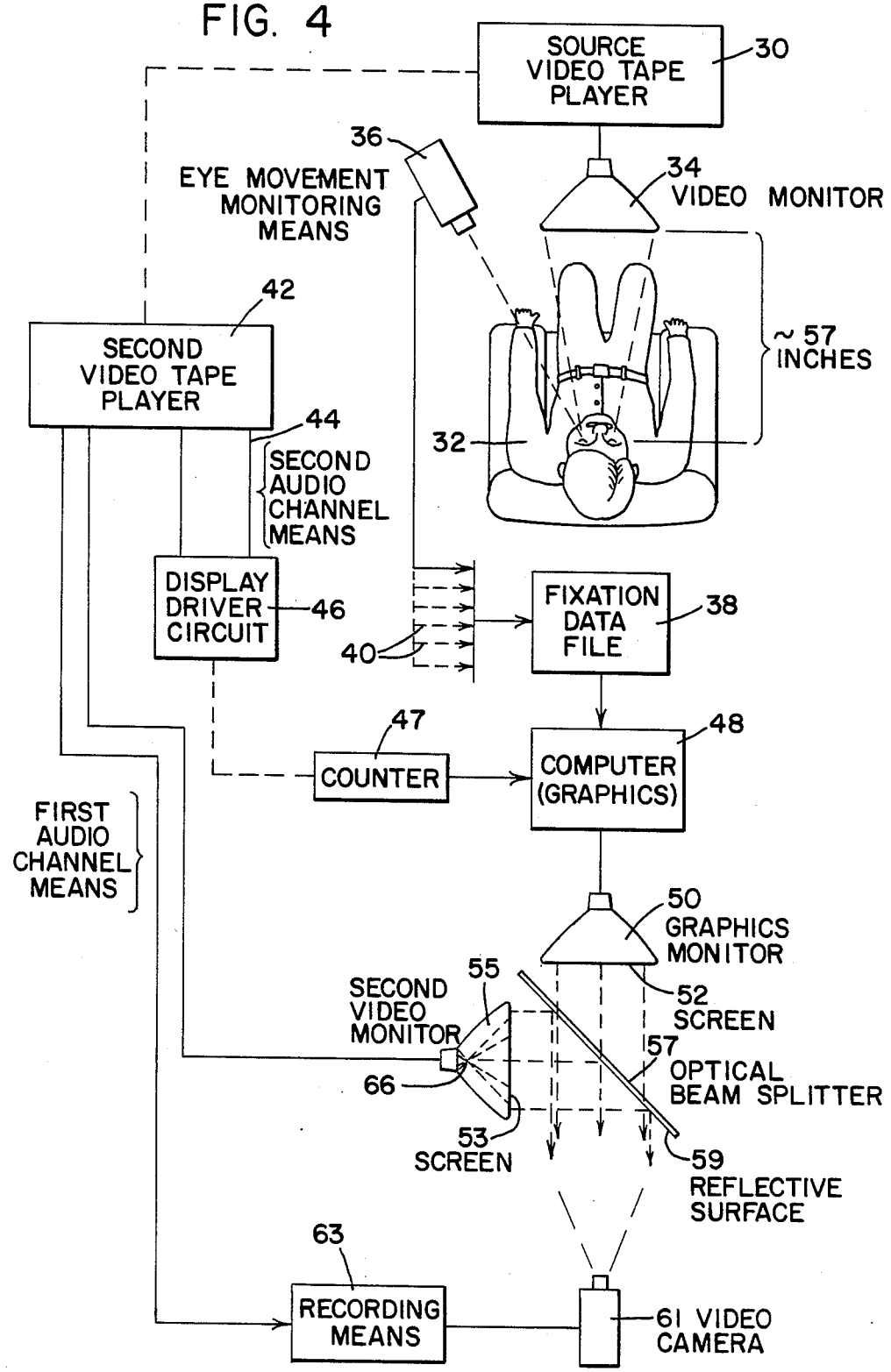
FIG. 4 is a diagram illustrating the overall combination of apparatus which forms a preferred embodiment of the system of the present invention.

The overall combination of apparatus which forms a preferred embodiment of the system of the present invention is shown in FIG. 4. Accordingly, a source video player 30 is provided for playing a tape of the subject commercial to the viewing individual 32 by means of a 24 inch diagonal monitor 34. The viewing individual 32 is seated comfortably about 57 inches in front of the color video monitor 34. A complete eye movement monitoring system 36 is disposed so as to continually monitor the eye movement of the viewing individual 32. Visual fixation data, consisting of start time, duration and X Y coordinates are extracted from the raw eye movement measurements. These fixation data are stored in a fixation data file 38. This fixation data file 38 is used to compile such data from a number of test individuals as indicated by the numerous input arrows shown 40. A second video player 42 is then provided to reply the video taped commercial, such video player being further provided with a second audio channel means 44 whereby an audio tone is generated to mark the beginning of the replaying of the subject commercial. Upon sensing of this tonal signal of the second audio channel means 44, a display driver circuit 46 begins to derive, from the video presentation, a series of vertical synchronizing pulses. These vertical synchronizing pulses then trigger a counter 47 which, upon each eighth vertical pulse, will generate an electrical signal. Upon sensing of such signal the computer 48 will replot fixation data from the cumulative fixation data file 38 on a computer graphics monitor 50 thereby maintaining real time synchrony with the source video. In this preferred embodiment, the computer graphic monitor 50 is positioned so that its screen 52 is perpendicular to the screen 53 of a second color video monitor 55. An optical beam splitter 57 is positioned angularly between the screen of graphics monitor 53 such that the reflected surface 59 of said beam splitter 57 is positioned toward a video camera 61. The video camera 61 is provided with a recording device 63. The image of the computer graphics monitor 50 is projected through the beam splitter 57 while the image of second source video monitor 55 is reflected from the front surface of the beam splitting plate 57. Thus, the optical images displayed by the two monitors 50, 55 are combined by the beam splitter 57. It should be appreciated that the reflective surface of the beam splitting plate 57 will result in the projection of a mirror image of that displayed on screen 53. Therefore, the image of the commercial being displayed by screen 53 is inverted as shown by dotted lines 66. This is readily achieved by electrically inverting the deflection yoke of the cathode ray tube of the second video monitor 55. Thus, the horizontally inverted image of screen 53 will be reflected from beam splitting plate 57 as a true image of the television commercial as it was originally perceived by the viewing individual 32. The optically combined images of the computer graphics monitor 50 and second video monitor 55 are then recorded by video recording device 63 through camera 61. This composite recording is then available for subsequent evaluation.

Figure 5:
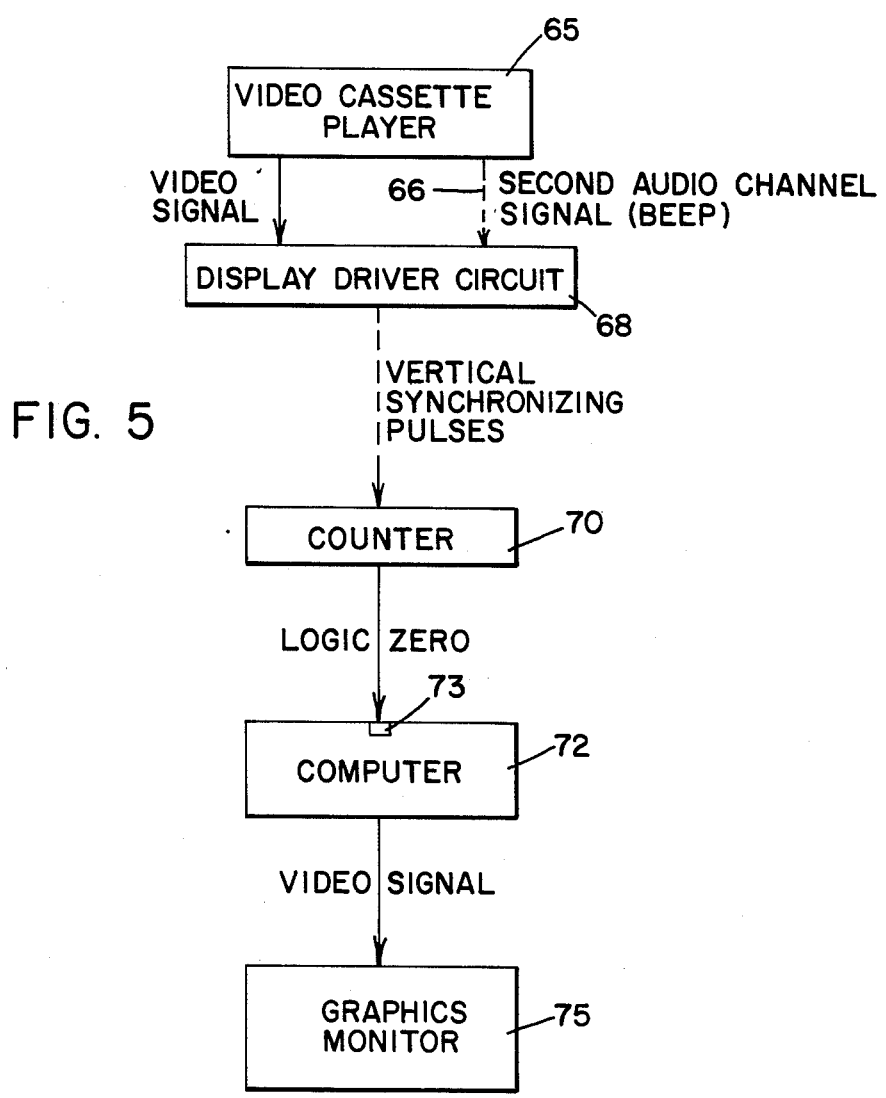
FIG. 5 is a diagram illustrating a further aspect of the present invention whereby the time-synchronized visual fixation data are plotted and mixed with a subject visual or audiovisual presentation to provide a composite video display; and, FIG. 6 is a view of a single scene from a television commercial with subgroup specific visual fixation points superimposed thereupon.

FIG. 5 is a block diagram detailing a preferred combination of apparatus by which real time synchrony is maintained between the dynamic visual fixation point display and the subject video presentation. A video cassette player 65 is used to replay the subject video presentation. The video cassette player 65 is further provided with a second audio channel 66. An audio signal such as a beep is provided over said second audio channel 66 to mark the beginning of the subject video presentation. Upon sensing of this audio signal, a specialized display driver circuit 68 accepts the video signal from the video cassette/recorder 65. The display driver circuit 68 derives therefrom a series of vertical synchronizing pulses which in turn trigger counter 70. Thus, on the sensing of each eighth vertical synchronizing pulse the counter 70 will generate a logic zero. Accordingly, a logic zero is generated every fourth TV frame (i.e. 2 vertical sync pulses per frame×4 frames). The counter 70 is operatively connected to a computer 72 through an input port 73. The computer 72 is adapted to poll the input port 73 for the periodic logic zero generated by counter 70. Upon sensing the periodic logic zero coinsiding with each fourth frame of the subject video, the computer 72 is adapted to plot the appropriate visual fixation points and to display such point plots on a video monitor 75. Thus, by the above-described combination of apparatus, real time synchrony is maintained between the video signal of the video cassette player 65 and the fixation point plot display on video monitor 75.

Figure 6:
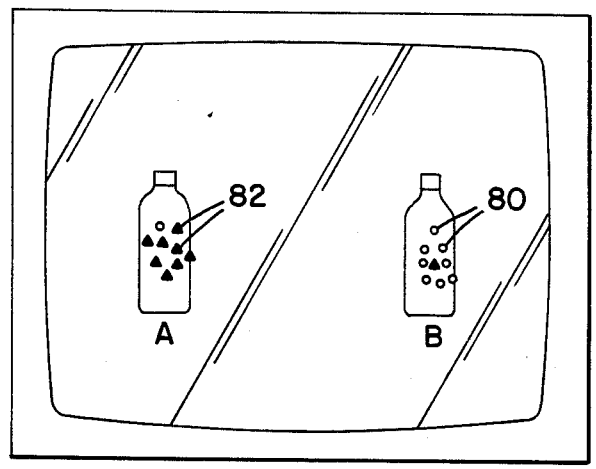

It must be further appreciated that the method and system of the present invention is adaptable to plot individual viewer fixation points in a manner that will enable the evaluator to readily determine the particular subgroup to which each viewer fixation point belongs. Such subgroups may be based upon any criteria, including demographic criteria such as age of viewer, sex, geographic domicile, etc. For example, FIG. 6 shows a single frame on a composite video tape wherein the points of visual fixation are divided into viewer subgroups. Specifically, FIG. 6 depicts two products, product A and product B, with viewer fixation points superimposed thereupon. The fixation points of male viewers are plotted as open circles 80 while the fixation points of female viewers are plotted as solid triangles 82. In this manner, it is discernible from the scene shown that eight of nine fixation points on product A were those of females while eight of nine fixation points on product B were those of males. Accordingly, the evaluator of the composite display shown in FIG. 6 may draw conclusions as to the looking response of males versus females with regard to products A and B.

The display driver circuit used in practicing the present invention triggers serial replotting of the graphic fixation point display, via the attendant computer, at precise intervals which maintain real time synchrony between the displayed data and the subject video presentation.

Figure 7A:
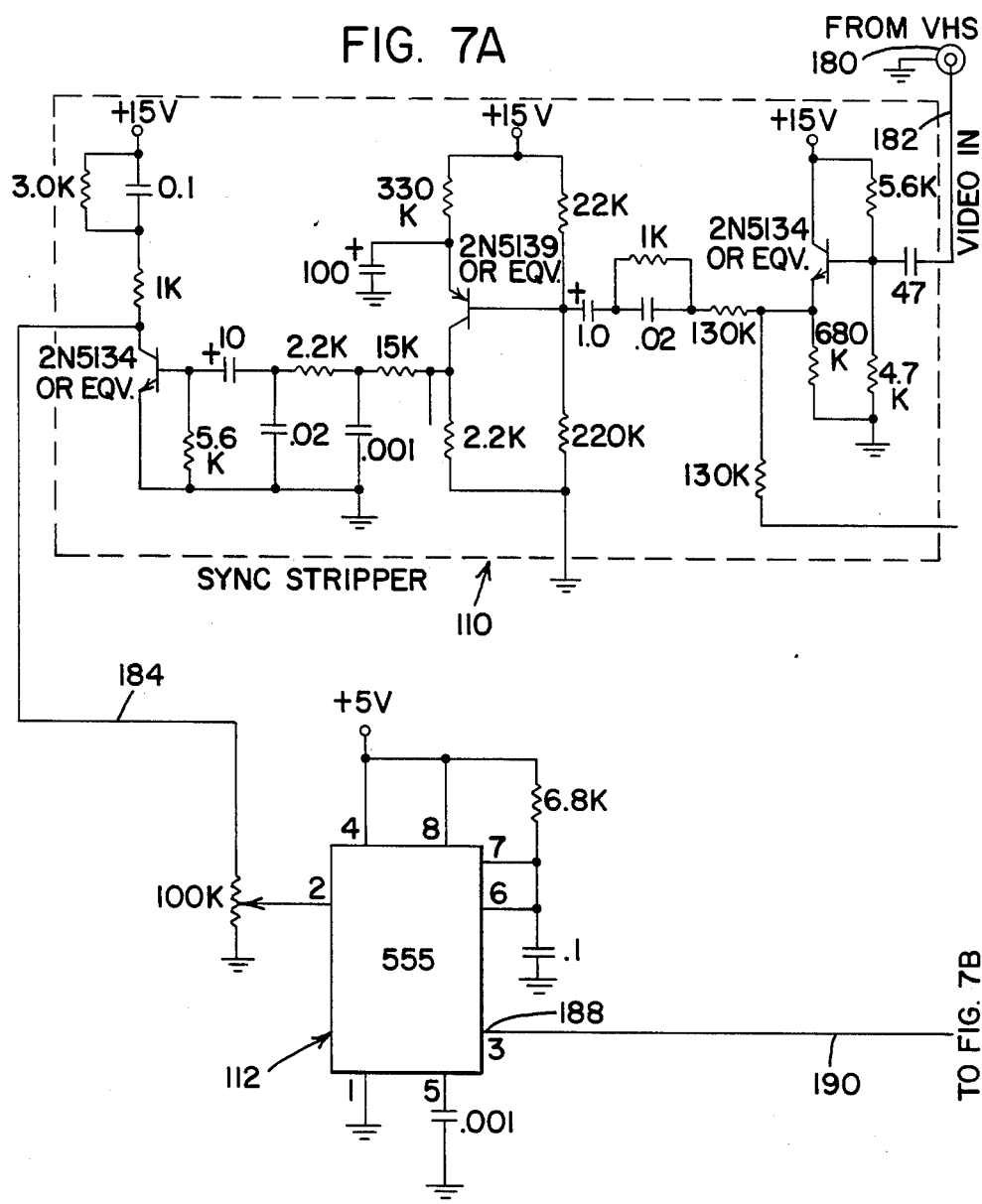
FIG. 7 is a schematic electrical diagram of the display driver circuit of the present invention.
Figure 7B:
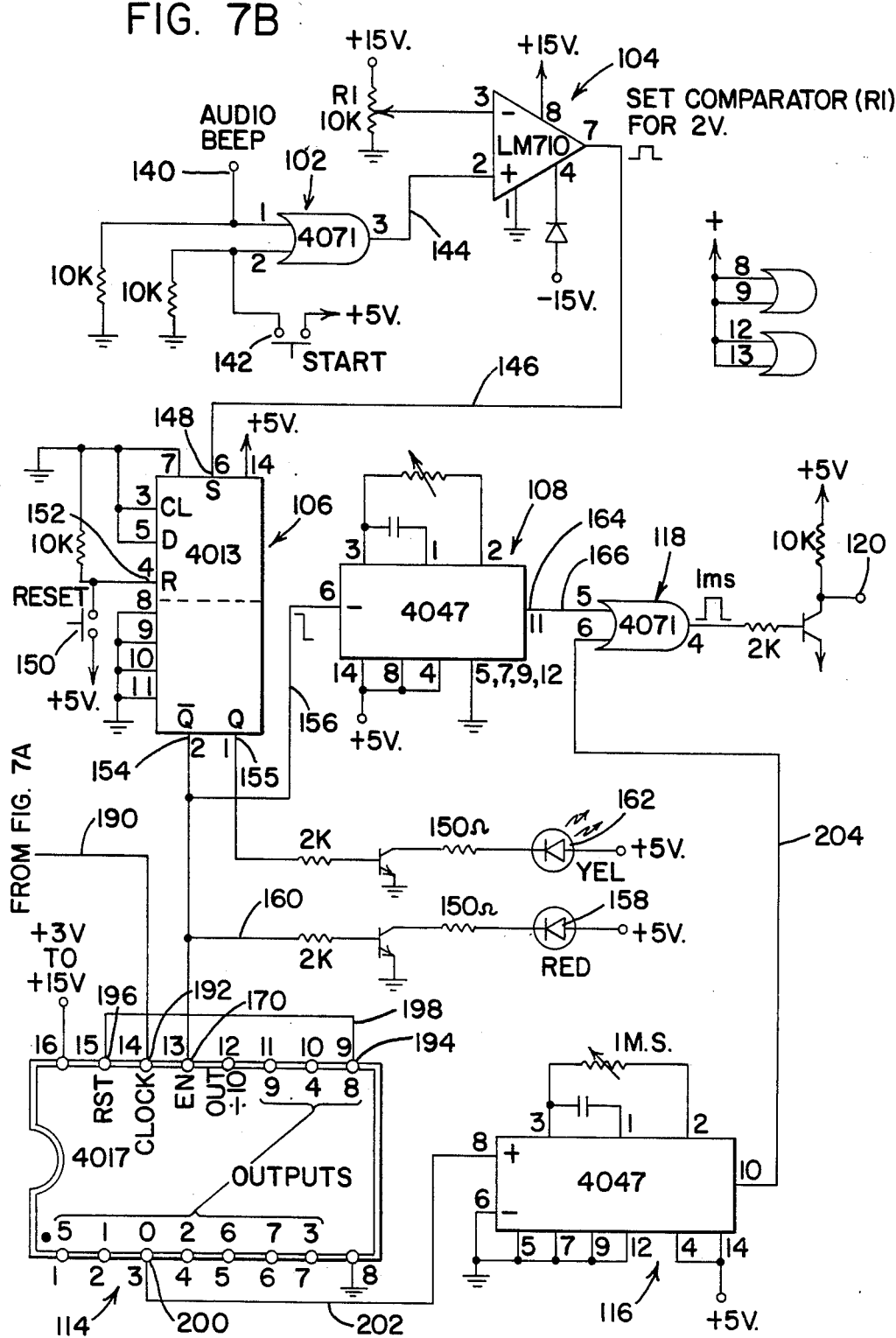

FIG. 7A and B is a schematic representation of a preferred embodiment of the display driver circuit. The circuit, as shown in FIG. 7, includes three major subcircuits: (1) an initiator/reset subcircuit, (2) a pulse counting subcircuit and, (3) a terminal subcircuit.

The initiator/reset subcircuit consists of a first ORgate 102, a comparator 104, a dual D flip flop 106, and a first pulse generator 108.

The pulse counting subcircuit consists of a sync pulse stripper 110, a monostable timer 112, a decade counter 114 and a second pulse generator 116.

The terminal subcircuit is simply a second ORgate 118 which compares the signals received from the initiator/reset and pulse counting subcircuits. Terminal ORgate 118 is connected to a terminal connector 120 which inputs to the computer. The computer is programmed to replot the graphic display each time the display circuit generates a logic zero at terminal connector 120.

To initially trigger the display driver circuitry, the initiator/reset subcircuit may be activiated by either the second audio signal of the subject video tape 140 or ON button 142. Audio signal input 140 and ON button 142 are each connected to a different input of ORgate 102. Thus, either depression of ON button 142 or sensing of audio signal 140 will result in output of a logic 1 from ORgate 102, through line 144, to the non-inverting input arm of comparator 104. Comparator 104, upon sensing the output received from ORgate 102, generates a 2 volt square wave. This signal is applied to SET pin 148 of D type flip flop 106 by line 146. In addition, reset button 150 is connected to the RESET connector 152 of flip flop 106. A positive input from ORgate 102 via SET connector 148 will force $\bar{Q}$ to logic 1 and Q to logic 0. Conversely, a logic 1 input at RESET connector 152 forces $\bar{Q}$ to logic 0 and Q to logic 1. The $\bar{Q}$ output 154 of flip flop 106 is connected to pulse generator 108 by line 156 and to a red panel light 158 through line 160. Q output 155, on the other hand, is connected to a yellow panel light. In response to either the audio or manual start signal, flip flop 106 goes to $\bar{Q}$ logic 0 and Q logic 1. Upon receiving the Q output from flip flop 106, pulse generator 108 generates a 1 ms signal at output 164. Output 164 is connected to terminal ORgate 118 via line 166. Thus, when the initiator/reset subcircuit is triggered, a logic one will briefly appear at terminal ORgate 118. This results in a logic 0 at terminal connector 120 and triggers the initial display of the computer graphics.

In addition, the $\bar{Q}$ output 154 of flip flop 106 is connected to the enable pin 170 of decade counter 114. Input at the enable pin must be ground in order for the counter to function. Therefore, when $\bar{Q}$ goes to ground in response to the start signal, the decade counter of the pulse counting subcircuit is simultaneously enabled.

The pulse counting subcircuit accepts, from a source video tape player, a video signal at video input connector 180. The beginning of the video signal is, of course, coincidental with the activation of audio input 140 or start button 142. Upon receiving the subject video signal via line 182, sync stripper 110 derives and transmits only the vertical synchronization pulse generated by each field of the video signal. These vertical synchronization pulses travel via line 184 to trigger monostable timer 112. Upon each fall in pulse voltage from above 2 V to below 2 V, timer 112 is triggered to generate an output pulse. The width of each pulse generated by timer 112 is determined by R=6.8 k and C=1 pF as shown. The output pin 188 of timer 112 is connected to the clock pin 192 of decade counter 114. When enable input 170 and reset input 115 are at ground (after triggering of the initiator/reset subcircuit), counter 114 will advance one count as it senses each ground to positive transition received from timer 112 via line 190. Upon each eighth such transition, the "8" output 194 of counter 114 goes from ground to positive. This "8" output pin is connected to counter reset pin 196 by line 198. Thus, when the "8" output goes positive, the reset input, likewise, goes to positive and the counter returns to zero. In this state, the "0" output 200 of counter 114 becomes positive while the others remain at ground. The 0 output 200 is connected to pulse generator 116 via line 202. Thus, upon each positive "0" output from counter 114, pulse generator 116 will emit a 1 mv signal. The signal emitted by pulse generator 116 travels along line 204 to terminal ORgate 118. Upon receiving an input of logic 1 from either the initiator/reset subcircuit via line 204, or the pulse counting subcircuit via line 116, the output of terminal ORgate 118 will be at logic 1 for a period of 1 ms. This results in a 1 ms logic 0 at terminal connector 120. The computer to which terminal connector 120 is connected is programmed to continuously poll connector 120 for a logic 0. Upon each sensing of a logic 0 at terminal connector 120 the computer is further programmed to update the graphic display of visual fixation points. Accordingly, initial plotting of the data occurs upon depression of the audio signal sensor (initiator/reset subcircuit) and replotting occurs, repeatedly, upon the detection of each eighth vertical synchronization pulse (pulse counting subcircuit) of the subject video presentation. It is by this method that the display driver circuit maintains temporal synchrony with the subject video.

Additionally, the present invention may include numerous embodiments not specifically described herein but which will utilize the present method and system for analyzing the visual impressional characteristics of any video program containing a video signal which provides a sense of continuous visual displays, possibly having an audio signal synchronized therewith, and wherein said analysis occurs by first electronically determining and providing point of gaze data with the video signal to achieve a correlated set of points for each viewing individual. After repeating such steps to produce correlated sets of points for a given number of individuals, these correlated sets of points are then superimposed upon the video signal in the form of visual indicia such as darkened dots, such superimposition being made in a time-synchronized manner corresponding with known frames of the video signal.

Having thus described the invention, what is claimed is:

1. A method of generating and displaying visual fixation data obtained from two or more individuals viewing a visual presentation whereby points of visual fixation are superimposed, in real time synchrony, upon said visual presentation, such method comprising the steps of:
 (a) displaying a visual presentation to at least two of said viewer individuals;
 (b) dectecting an eye movement of each said viewing individual by measuring the eye point of gaze of said individuals to provide a point of gaze measurement for each individual;
 (c) extracting from each said point of gaze measurement a series of visual fixations, each such visual fixation being measured by its starting time, duration, and X and Y coordinates;
 (d) storing said series of visual fixation measurements in retrievable form;
 (e) displaying said series of visual fixation measurements in the form of a dynamic, graphic display of visual fixation measurements identified by visually discernible symbols;
 (f) superimposing, in real time synchrony, said graphic display of visual fixation symbols upon a recorded image of said visual presentation to form a composite display of said visual fixation symbols and said visual presentation; and,
 (g) providing means for distinguishing between the individual visual fixation measurements of said at least two individual viewers such that the graphically displayed symbols corresponding to one of said two viewers is visually distinguishable from the symbol corresponding to the other.

2. The method of claim 1 including the additional step of video taping said composite display of said visual fixation points and said visual presentation to thereby provide a real time synchronized, composite video tape for subsequent evaluation.

3. The method of claim 1 including the additional step of storing said graphic display of visual fixation points in retrievable form prior to the said superimposition thereof upon said recorded image of said visual presentation.

4. The method of claim 1 wherein the said visual presentation is a video display.

5. The method of claim 1 wherein an audio stimulus is provided concurrently with said visual presentation such that the said one viewing individual perceives both audio and visual stimuli while viewing the said visual presentation.

6. The method of claim 5 wherein the audio-visual stimulus is a television commercial.

7. The method of claim 2 wherein said composite video tape is evaluated to determine the effectiveness of said visual presentation in communicating specific information to said one or more viewing individuals.

8. The method of claim 2 wherein said composite video tape is evaluated to determine the desirability of adding, eliminating or otherwise editing the contents of said visual presentation in order to optimize the effectiveness of said visual presentation in communicating specific information.

9. The method of claim 1 wherein said point of gaze measurements are made by the pupil center-corneal reflection method.

10. The method of claim 1 wherein said graphic display of visual fixation points is superimposed upon said visual presentation by optical means whereby a first video monitor displaying said visual presentation is positioned so that its image display surface is perpendicular to and adjacent to the image display surface of, and directs its image display across the image display of, a second video monitor displaying said real time synchronized visual fixation points, with an optical beam splitting plate disposed at a 45° angle between said perpendicularly positioned image display surfaces so that the image from one of said monitors passes through said beam splitting plate while the corresponding image from the other one of said monitors is reflected from the opposite surface of said beam splitting plate such that the optical outputs of said first and second video monitors are combined to provide a real time synchronized composite image of said visual fixation points superimposed upon said visual presentation.

11. The method of claim 1 wherein said graphic display of visual fixation points is superimposed upon said visual presentation by time synchronized mixing of the output signal of a computer adapted to graphically plot said visual fixation points with the output signal of a video tape recorder replaying a video tape of said visual presentation to thereby provide a composite signal consisting of said visual presentation, said combined signal being storable for subsequent video projection of said composite display.

12. The method of claim 10 wherein the said composite image of said visual fixation points and said visual presentation is recorded on video tape for subsequent replay.

13. The method of claim 11 wherein said composite display of said visual fixation points and said visual presentation is recorded on video tape for subsequent replay.

14. A method of generating and displaying reduced visual fixation data obtained from individuals viewing a visual presentation wherein said reduced visual fixation data is superimposed, in real time synchrony, upon said visual presentation, said method comprising the steps of:

(a) providing a visually neutral viewing room with a video monitor positioned therewithin for displaying said visual presentation to one or more individuals;

(b) displaying said visual presentation to said one or more individuals in said room by way of said video monitor;

(c) directing a dimly visible beam of collimated near infrared light into the pupil of an eye of one of said individuals;

(d) positioning a video camera so as to record the pupil center and corneal reflection of the eye upon which the same beam of collimated near-infrared light is directed;

(e) providing a control unit operatively connected to said video camera and adapted to detemrine and provide raw eye position measurements of the point of gaze of said individual by monitoring for a measured time the vector between the pupil center and the point at which said beam of collimated near-infrared light rays reflects from the cornea of said eye of said individual;

(f) providing a computer adapted to extract from said raw eye position measurements a series of eye fixation variables, each such fixation being defined by its starting time and duration with respect to said measured time, and by its X and Y coordinates as spacially related to said video presentation, and further to reformant such eye fixation data to facilitate their storage in retrievable form;

(g) providing means adapted to provide said reduced fixation data in the form of a dynamic plot of said stored fixation data comprising successive discreet static fixation variables, said static fixation variables being rerieved from said stored data at predetermined intervals with respect to said measured time and having durations within said plot equal to said itnervals;

(h) providing a means for optically or electronically combining, in real time synchrony, said dynamic plot of said visual fixation points with said visual presentation to provide a real time synchronized composite display.

15. The method of claim 14, including the step of containing and partially concealing the source of said beam of near-infrared red light and camera within a common housing positioned within said visually neutral viewing room.

16. The method of claim 14 including providing a servo-controlled tracking mirror for automatically tracking the eye during lateral or vertical head motions of said one individual, said optical tracking mirror being operatively connected to said control unit so that said control unit will sense when the image of said pupil is no longer centered within the viewing angle of said video camera and said control unit will respond by signaling said servo-controlled tracking mirror to compensate for said vertical or lateral head movement by repositioning the reflected image of said pupil of said eye within the center of the image field of said video camera.

17. The method of claim 14 wherein real time synchronization of the said dynamic plots of said individual fixations with the said visual presentation is achieved by providing said computer with a logic zero source, such logic zero being generated by a display driver circuit specifically provided for such process.

18. The method of claim 17 wherein said driver circuit is adapted to derive from a video tape of said visual presentation a series of vertical syncrhonization pulses and to use such pulses to generate a periodic signal to trigger said computer to retrieve said fixations, thereby maintaining real time synchrony with said visual presentation while providing a dynamic display of discrete visual fixations.

19. A system for generating and displaying visual fixation data obtained from one or more individuals viewing a visual presentation whereby points of visual fixation are superimposed, in real time synchrony, upon said visual presentation, such system comprising, in combination, the elements of:
  (a) means for displaying a visual presentation to at least one of said viewing individuals;
  (b) means for detecting an eye movement of said one viewing individual by measuring the point of gaze of an eye of said individual to provide a series of point of gaze measurements;
  (c) means for extracting from said point of gaze measurements a series of visual fixations, each such visual fixation being defined by its starting time, duration and X and Y coordinates;
  (d) means for storing said series of visual fixation variables in rerievable form;
  (e) means for displaying said series of visual fixation points in the form of a dynamic, graphic display of visual fixation points; and,
  (f) means for superimposing, in real time synchrony, said graphic display of visual fixation points upon a recorded image of said visual presentation to form a composite display of said visual fixation points and said visual presentation, including means for maintaining real time synchrony between said visual presentation and said visual fixation point display, said means comprising a display driver circuit adapted to receive a series of vertical synchronizing pulses from a recording of said visual presentation, said display driver circuit being further connected to a counter adapted to count said vertical synchronizing pulses and to generate, upon each predetermined number of pulses, a logic zero signal, said counter being operatively connected to a computer adapted to receive said signal from said counter and further adapted to replot said visual fixation points upon each sensing of said signal.

20. The system of claim 19 including the additional element of a means for video taping said composite display of said visual fixation points and said visual presentation to thereby provide a real time synchronized, composite video tape for subsequent evaluation.

21. The system of claim 19 including the additional element of a means for storing said graphic display of visual fixation points in retrievable form prior to said superimposition thereof upon said recorded image of said visual presentation.

22. The system of claim 19 wherein said means for displaying a visual presentation comprises a video tape player operatively connected to a color video monitor.

23. The system of claim 19 wherein said means of detecting eye movement of said viewing individual comprises an eye movement monitor which is adapted to measure said point of gaze by said pupil center-corneal reflection method.

24. The system of claim 19 wherein said means for extracting from said point of gaze measurements a series of visual fixations is operatively combined with said means for detecting eye movement.

25. The system of claim 19 wherein said means for storing said series of visual fixation variables is operatively connected to a computer adapted to display such variables in a graphic manner.

26. The system of claim 19 wherein the means for displaying said visual fixation points is an appropriately adapted computer operatively connected to a color graphics monitor.

27. A system for analyzing the visual impressional characteristics of a video program containing a video signal occuring at a rate providing a sense of continuous visual displays with a given display area and an audio signal synchronized with said visual display, said system comprising:
  (a) means for electronically providing a set of points of gaze for an individual, each point of gaze correlated to locations on said display area of said visual display for a known frame;
  (b) means for electronically correlating said points of gaze for said individual with said video signal as a correlated set of points of gaze;
  (c) means for repeating steps (a) and (b) for many individuals to produce many correlated sets of points of gaze each correlated with said video signal;
  (d) means for superimposing said correlated sets onto said video signal by creating a visual indicia of each point of gaze of each individual onto the known frames of said visual signal; and,
  (e) means for displaying said visual signal with said superimposed points of gaze displayed as said indicia of said known frames.

28. A system as defined in claim 27 wherein said known frame is at least each fourth frame.

29. A system as defined in claim 27 wherein said indicia is a visually displayed dot.

30. A method of analyzing the visual impressional characteristics of a video program containing a video signal occuring at a rate providing a sense of continuous visual displays with a given display area and an audio signal synchronized with said visual display, said method comprising:
  (a) electronically providing a set of points of gaze for an individual, each point of gaze correlated to locations on said display area of said visual display for a known frame;
  (b) electronically correlating said points of gaze for an individual, each point of gaze correlated to locations on said display area of said visual display for a known frame;
  (c) repeating steps (a) and (b) for many individuals to produce many correlated sets of points of gaze each correlated with said video signal;
  (d) superimposing said correlated sets onto said video signal by creating a visual indicia of each point of gaze of each individual onto the known frames of said visual signal; and,
  (e) displaying said visual signal with said superimposed points of gaze displayed as said indicia of said known frames.

31. A method as defined in claim 30 wherein said known frame is at least each fourth frame.

32. A method as defined in claim 30 wherein said indicia is a visually displayed dot.

* * * * *